United States Patent [19]
Chan

[11] Patent Number: 5,233,084
[45] Date of Patent: Aug. 3, 1993

[54] METHOD FOR PREPARING Alpha-ARYLPROPIONIC ACIDS

[75] Inventor: Albert S. C. Chan, St. Louis, Mo.

[73] Assignee: Monsanto Company, St. Louis, Mo.

[21] Appl. No.: 620,672

[22] Filed: Dec. 3, 1990

Related U.S. Application Data

[63] Continuation-in-part of Ser. No. 487,465, Mar. 2, 1990, which is a continuation-in-part of Ser. No. 369,875, Jun. 22, 1989, Pat. No. 4,994,607.

[51] Int. Cl.$^5$ .............................................. C07L 62/06
[52] U.S. Cl. ................................... 562/466; 562/496
[58] Field of Search ........................... 562/466, 496

[56] References Cited

U.S. PATENT DOCUMENTS

| | | | |
|---|---|---|---|
| 3,637,767 | 1/1972 | Alvarez | 424/308 |
| 3,998,966 | 12/1976 | Fried et al. | 424/308 |
| 4,008,281 | 2/1977 | Knowles et al. | 260/606.5 P |
| 4,142,992 | 9/1977 | Knowles et al. | 252/431 |
| 4,207,241 | 6/1980 | Fried et al. | 260/345 |
| 4,239,914 | 12/1980 | Campolmi et al. | 562/466 |
| 4,328,356 | 5/1982 | Giordano et al. | 560/56 |
| 4,409,397 | 10/1983 | Paxson | 562/496 |
| 4,542,237 | 9/1985 | Schlowmer | 562/466 |
| 4,601,797 | 7/1986 | Wagenknecht | 204/59 |
| 4,691,037 | 9/1987 | Yoshikawa et al. | 566/18 |
| 4,766,225 | 8/1988 | Sayo et al. | 566/16 |
| 4,857,462 | 8/1989 | Maier et al. | 435/197 |
| 4,994,607 | 2/1991 | Chan | 562/496 |

FOREIGN PATENT DOCUMENTS 0272787 6/1988 European Pat. Off. .
59-51234 3/1984 Japan .

OTHER PUBLICATIONS

NATO ASI Series, Series E, Applied Sciences, No. 103, Martinns Nijhoff Pub. (1986).
Asymmetric Synthesis, vol. 5, Chiral Catalysis, pp. 81–83.
J. Chem. Soc., Chem. Commun., Sep. 1989, p. 1208.
Ojima et al, J. Org. Chem., 45, No. 23, 4728 (1980).
Takahashi et al, Chemistry Letters, 1921 (1987).
Piccolo et al, J. Org. Chem., 52, 10 (1987).
Noyori et al, J. Am. Chem. Soc., 109, 5856 (1987).

Primary Examiner—Paul J. Killos
Attorney, Agent, or Firm—Kenneth D. Goetz; Paul L. Passley; James C. Bolding

[57] ABSTRACT

Process for preparing α-arylpropionic acids by catalytically asymmetrically hydrogenating α-arylpropenoic acids prepared from α-aryl ketones.

15 Claims, No Drawings

METHOD FOR PREPARING Alpha-ARYLPROPIONIC ACIDS

This is a continuation-in-part of U.S. patent application Ser. No. 07/487,465, filed Mar. 2, 1990, which is a continuation-in-part of U.S. patent application Ser. No. 07/369,875, filed Jun. 22, 1989, now U.S. Pat. No. 4,994,607

BACKGROUND OF THE INVENTION

1. Field of the Invention

The present invention relates to a novel synthetic route for preparing α-arylpropionic acids, e.g., 2-(6'-methoxy-2'-naphthyl)propionic acid (naproxen) and 2-(p-isobutylphenyl)propionic acid (ibuprofen), and to intermediates prepared and utilized in such synthetic route.

2. Prior Art

Naproxen is a nonsteroidal compound having anti-inflammatory, nonnarcotic analgesic and antipyretic activities. It belongs to a group of compounds, generally classified as arylpropionic acids or arylalkanoic acids, which group includes naproxen, ibuprofen, ketoprofen, fenoprofen, suprofen, flurbiprofen, benoxaprofen, pirprofen and carprofen. Each of the compounds of this group are related in that they are propionic acid derivatives.

Many synthetic routes for producing arylpropionic acids and, in particular, naproxen have been proposed. The first synthetic routes produced a mixture of optical isomers or enantiomorphs. Thus, such routes required resolution of the mixture to obtain the more active isomer, such as with cinchonidine or glucamine. These resolution procedures, however, require numerous recrystallizations and are, therefore, not commercially attractive.

More recently, attempts have been made for preparing the pharmaceutically useful optical isomer in excess of the physiologically inactive isomer so that the resolution procedure could be simplified. For example, U.S. Pat. No. 4,542,237 discloses a process for preparing α-arylpropionic acids and, in particular, a process for preparing naproxen, which involves a noncatalytic rearrangement of a ketal or thioketal of 2-hydroxy-1-(6'-methoxy-2'-naphthyl)propan-1-one by activating the α-hydroxy moiety with an esterifying agent to form the corresponding alkyl aryl ketal or thioketal ester substrate. Concomitant or sequential hydrolysis of the ester produces the corresponding arylpropionic acid, 2-(6'-methoxy-2'naphthyl)propionic acid. See also Piccolo et al, J. Org. Chem. 52, 10–14 (1987), and references cited therein. In the majority of cases, however, production of the desired isomer in enantiomeric excess has been limited and numerous recrystallizations are still required.

Asymmetric hydrogenation of arylpropenoic acids has been previously proposed as a method of further increasing the enantiomeric excess of the desired isomer. However, these procedures have had limited success in producing the desired optical isomer in enantiomeric excess sufficient to significantly simplify the resolution procedures. For example, Campolmi et al, U.S. Pat. No. 4,239,914 discloses catalytic asymmetric hydrogenation of 2-(6'-methoxy-2'-naphthyl)propenoic acid utilizing a chiral bidentate phosphine complex. Preferred compounds include 1,2-ethanediylbis(o-methoxyphenyl)phenylphosphine (DIPAMP), [2,3-0-isopropylidene-2, 3-dihydroxy-1,4-bis(diphenylphosphine)butane] (DIOP) and N,N'-bis-((+)-~-methylbenzyl)-N,N'-bis-(diphenylphosphine)ethylenediamine (PNNP). The catalytic asymmetric hydrogenations are conducted with a DIOP catalyst at a temperature of 25° C. and at $H_2$ pressures of and 3.5 atmospheres (~15 p.s.i. and ~52 p.s.i., respectively) and at 50° C. and 3.5 atmospheres. Such a hydrogenation is also conducted with a PNNP catalyst at 0° C. and 1 atm. Enantiomeric excess (e.e.) of the desired product is reported to be about 70% or less.

Although Campolmi et al disclose that the hydrogenation can be conducted at temperatures of between 0° C. and 70° C. and at pressures of between 1 and 50 atmospheres, it is reported in Asymmetric Catalysis, NATO ASI Series, Series E: Applied Sciences, pp. 24–26, B. Bosnich Editor, Martinus Nijhoff Publishers (1986) that in general catalytic asymmetric hydrogenations conducted at temperatures of less than about 25° C. and/or at pressures greater than about 15 psig $H_2$ result in decreased e.e.'s. See also Asymmetric Synthesis, Vol. 5—"Chiral Catalyst", pp. 60–62, J. D. Morrison, Editor, Academic Press, Inc. (1985).

It has now been discovered, contrary to the above teachings, that conducting asymmetric catalytic hydrogenations at temperatures below about 15° C. and, optionally, at $H_2$ pressures greater than about 5 atmospheres, (~75 psig) results in higher e.e.'s of the desired product such that resolution of the resulting optical isomer mixture is significantly simplified. It has also been discovered that higher e.e.'s can be obtained by conducting such hydrogenations at temperatures of up to about 30° C. in the presence of an organic base or utilizing a specific asymmetric hydrogenation catalyst.

For example, Noyori et al, J. Org. Chem. 52, 3174–76 (1987), disclose asymmetric hydrogenation of 2-(6'-methoxy-2'-naphthyl)propenoic acid with a catalytic amount of Ru[(S)-2,2'-bis(diphenylphosphino)-1,1'-binaphthyl]$(CH_3CO_2)_2$ at about 2000 psig $H_2$ and apparently, although not clearly, at 15°–30° C. to afford naproxen. However, it has now been discovered that utilizing this same catalyst at temperatures below about 15° C. and, optionally, at high $H_2$ pressures, significantly increases the enantiomeric excess of the desired isomer Furthermore, conducting the reaction in the presence of an organic base, even at temperatures up to about 30° C., significantly increases the enantiomeric excess of the desired isomer.

SUMMARY OF THE INVENTION

Accordingly, the present invention is directed to a process for preparing α-arylpropionic acids, and in particular for preparing naproxen and ibuprofen, wherein high enantiomeric excess of the desired optical isomer is produced. The present invention resides in increasing the enantiomeric excess of the desired product by conducting a catalytic asymmetric hydrogenation of the corresponding α-arylpropenoic acid at temperatures below or at about 30° C. under specific conditions. The novel process of this invention is particularly suited for preparing 2-(6'-methoxy-2'-naphthyl)propionic acid and 2-(p-isobutylphenyl)propionic acid. More particularly, the present invention is directed to an overall process for obtaining o-arylpropionic acids, particularly for obtaining naproxen and ibuprofen, and to intermediates prepared and utilized in such process. This overall process is characterized by catalytic asymmetric hydrogenation of a dehydration product of an acid treated electrochemically carboxylated aryl ketone.

DETAILED DESCRIPTION OF THE INVENTION

As stated above, the present invention resides in the discovery that α-arylpropenoic acids, such as 2-(6'-methoxy-2'-naphthyl)propenoic acid, can be converted to the corresponding α-arylpropionic acid in unexpected enantiomeric excess utilizing an asymmetric hydrogenation catalyst at low temperatures and, optionally, at high H₂ pressures. Examples of α-arylpropenoic acids useful in the present invention include those represented by the formula:

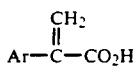

wherein Ar is selected from p-isobutylphenyl, 6-chlorocarbazyl-2, 3-phenoxyphenyl, 2-isopropylindanyl-5, 2-fluoro-4-biphenyl and 6-methoxy-2-naphthyl. A preferred α-arylpropenoic acid is 2-(6'-methoxy-2'-naphthyl)propenoic acid.

The α-arylpropenoic acids useful in the present invention can be prepared according to well-known procedures. A preferred procedure involves dehydration of an acid-treated electrochemically carboxylated α-aryl ketone corresponding to said α-arylpropenoic acid.

The α-aryl ketones are prepared by methods well known in the art. For example, 2-acetyl-6-methoxynaphthalene can be prepared utilizing a Friedel Crafts acylation reaction with 2-methoxynaphthalene as starting material.

A method for electrochemically carboxylating the α-aryl ketones, as well as subsequent acid treatment, is described in detail in U.S. Pat. No. 4,601,797 which is hereby incorporated by reference. In general, the reaction involves electrolyzing an aryl ketone at a cathode in the presence of carbon dioxide and in an electrolysis medium to effect addition of carbon dioxide to the aryl ketone. The electrochemically carboxylated aryl ketone is then treated with acid to produce the corresponding 2-aryl-2-hydroxypropionic acid. This reaction is conducted at a pressure (CO₂) of from about 1 atm to about 30 atm, preferably from about 1 atm to about 10 atm, most preferably at about 5 atm. The temperature at which the reaction is conducted depends on the pressure (CO₂) that is utilized. At the preferred pressure of 5 atm, the preferred temperature can range from about −5° to 40° C., preferably, 40° C. At lower pressures the temperature can range from about −10° C. to about 10° C., preferably 0° C.

The 2-aryl-2-hydroxypropionic acids are then dehydrated by well-known dehydration techniques to produce the corresponding α-arylpropenoic acid. One of such dehydration techniques involves utilization of a suspension of fused potassium acid sulfate in chlorobenzene at 130° C. for about 15 hours. Other solid catalysts such as KHSO₄ (other than fused), polymer-bound sulfonic acids (resins) and the like, may also be utilized.

To increase the rate of reaction, the chlorobenzene may be replaced with dichlorobenzene and the reaction conducted at 150°–160° C. for two to three hours. Other solvents such as organic solvents with boiling points above about 100 C which will not react with the catalyst and substrate of the arylpropenoic acid may also be utilized. To achieve high yields of the desired product, small amounts, such as about 100 ppm to about 10,000 ppm, based on the amount of 2-aryl-2-hydroxypropionic acid, of a free radical scavenger may be utilized. Exemplary free radical scavengers include 2,6-di-t-butyl-4-methyl phenol, substituted and unsubstituted hydroquinones, dilauryl thiodipropionate and the like. A preferred scavenger is 2,6-di-t-butyl-4-methyl phenol. Such free radical scavengers can be used, alone or in combination.

The most preferred dehydration technique is novel and produces α-arylpropenoic acids in high yield and with very little or no discoloration. This technique involves utilization of a solvent system which includes a low molecular weight carboxylic acid, such as, for example, acetic acid or propionic acid. The low molecular weight carboxylic acid, while serving as a solvent, also serves as the dehydration catalyst The solvent system can include other solvents as well, such as, for example, xylene, toluene, benzene and the like The α-arylpropenoic acids are then asymmetrically hydrogenated utilizing an asymmetric hydrogenation catalyst at low temperatures. The hydrogenation reaction is conducted at a temperature below about 15° C., preferably below about 10° C. such as below or at about 5° C. The lower limit on the temperature at which the reaction is conducted is not critical as the temperature can be as low as −15° C. with excellent results in terms of high enantiomeric excess of the desired product.

Optionally, the hydrogenation reaction can be conducted at high pressure. Preferably, the hydrogenation reaction is conducted at H* pressure above about 65 psig such as above about 75 psig, for example, at 1000 psig H*. The upper limit on the hydrogen pressure is not critical, however, such upper limit will depend on the capability of the equipment being utilized.

Examples of suitable asymmetric hydrogenation catalysts include rhodium (Rh) and ruthenium (Ru) complexes of chiral phosphine compounds. Such catalysts are described in Asymmetric Synthesis, Volume 5—"Chiral Catalyst" (1985), and Asymmetric Catalysis, NATO ASI Series, Series E. (1986), both of which are referenced above. More particularly, DIPAMP-type catalysts are disclosed in U.S. Pat. No. 4,142,992 to W. S. Knowles et al. Preparation of the bis phosphine compounds is disclosed in U.S. Pat. No. 4,008,281, also to W S. Knowles, et al. Optically active binaphthyl compounds are more particularly disclosed in Noyori et al, *J. Am. Chem. Soc.*, 109, 5856-58 (1987) and *J. Org. Chem.* 52, 3174-76 (1987), as Well as optically active bisphosphine catalysts (DIOP-type catalysts) more particularly disclosed in U.S. Pat. No. 4,142,992.

Thus, a suitable asymmetric hydrogenation catalyst is one selected from the group consisting of a) a rhodium or ruthenium complex having optically active bis phosphine compounds of the formula

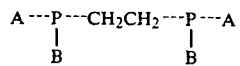

wherein A and B each independently represent substituted and unsubstituted alkyl radicals having from 1 to about 12 carbon atoms, substituted and unsubstituted cycloalkyl radicals having from about 4 to about 7 carbon atoms, and substituted and unsubstituted aryl radicals; provided that such substituents provide no significant interference with the steric requirements around the phosphorus atom, and A and B are different, b)

optically active bisphosphine binaphthyl compounds of the formula Ru(BINAP)(OCOR)$_2$ and Ru$_x$H$_y$Cl$_z$(BINAP)$_2$(S)$_p$ wherein BINAP represents a tertiary phosphine of the formula:

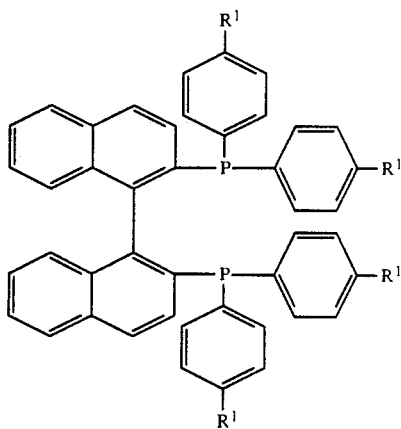

in which R represents substituted and unsubstituted alkyl radicals having from 1 to about 6 carbon atoms, substituted and unsubstituted halogenated alkyl radicals having from 1 to about 6 carbon atoms, substituted and unsubstituted aryl radicals, and substituted and unsubstituted aralkyl radicals; R$^1$ represents hydrogen, substituted and unsubstituted alkyl radicals having 1 to about 6 carbon atoms and substituted and unsubstituted aryl, aralkyl and alkaryl radicals, S is a tertiary amine and when y=o, x=2, z=4 and p=0 or 1, when y=1, x=1, z=1 and p=0; c) Rh or Ru catalysts containing chiral phosphines represented by the formula:

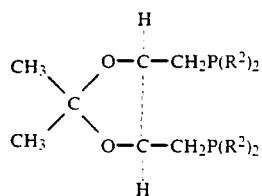

wherein R$^2$ represents substituted and unsubstituted alkyl radicals having from 1 to about 12 carbon atoms, substituted and unsubstituted cycloalkyl radicals having from about 4 to about 7 carbon atoms and substituted and unsubstituted aryl, aralkyl and alkaryl radicals; and d) phosphine complexes represented by the formulas:

Ru[L](OCOR$^3$)$_2$ and Ru$_x$H$_y$Cl$_z$[L]$_2$(S)$_p$ wherein L represents a phosphine of the formula:

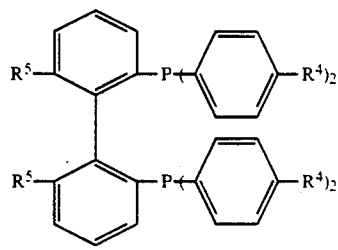

wherein R$^3$ represents substituted and unsubstituted alkyl radicals having from 1 to about 6 carbon atoms, substituted and unsubstituted halogenated alkyl radicals having from 1 to about 6 carbon atoms, substituted and unsubstituted aryl radicals and substituted and unsubstituted aralkyl and alkaryl radicals; R$^4$ represents H, substituted and unsubstituted alkyl radicals having 1 to about 6 carbon atoms and substituted and unsubstituted alkoxy radicals having 1 to about 6 carbon atoms; R$^5$ represents alkyl radicals having from 1 to about 6 carbon atoms and substituted and unsubstituted aryl radicals, S is a tertiary amine and when y=0, x=2, z=4 and p=0 or 1 and when y=1, x=1, z=1 and p=0. Many other asymmetric hydrogenation catalysts are well-known in the art and it is contemplated that such catalysts can also be utilized in the present invention with similarly improved results. A preferred catalyst is an optically active ruthenium binaphthyl compound, preferably the chloro derivative rather than the acetate Exemplary catalysts include [RuCl$_2$(BINAP)]$_2$(NEt$_3$), RuHCl(BINAP)$_2$, Ru(BINAP)(BF$_4$)$_2$. Additional exemplary binaphthyl catalysts include those prepared by reacting a ruthenium chloride complex with a binaphthyl ligand. Further exemplary catalysts include those wherein the chloride ligand is replaced with BF$_4-$, ClO$_4-$, PF$_6-$ or BPh$_4-$, and/or those wherein the binaphthyl ligand is replaced with a biaryl ligand. These types of catalysts are disclosed in U.S. Pat. No. 4,766,225 as not being satisfactory in terms of the optical yield attained. However, it has now been discovered that utilization of such catalysts for catalytic hydrogenation of α-arylpropenoic acids produces the corresponding α-arylpropionic acids in extremely high enantiomeric excess.

The catalytic hydrogenations utilizing such catalysts are conducted according to known conventional techniques in a homogeneous system which includes the catalyst, an organic solvent and, optionally, a base, preferably an organic base such as a nitrogenous base, for example, triethylamine, tributylamine and other organic amines, preferably other tertiary amines. Examples of suitable inorganic bases include sodium hydroxide and potassium hydroxide. The use of a base, particularly in conjunction with a ruthenium catalyst, serves to increase the enantiomeric excess of the α-arylpropionic acid. It has been found that when a base is employed with a ruthenium catalyst satisfactory results with respect to enantiomeric excess are obtained when temperatures as high as about 30° C. are employed However, in essentially all cases it is preferred to use below about 15° C. temperatures.

The catalyst/substrate molar ratio may vary between about 1:20 and about 1:20,000 preferably about 1:100 to about 1:10,000. A preferred catalyst/substrate molar ratio is about 1:10,000. The substrate/nitrogenous base molar ratio may vary between about 100:1 and about 1:5, preferably about 10:1 to about 1:1. The substrate/solvent ratio may vary between about 1:10,000 and about 1:1 by weight, preferably about 1:100 and about 1:3. These catalysts can be utilized in the form of complexes of a bis olefin, an arene or coordinated solvents.

Ruthenium complex catalysts of the formula:

[Ru(BINAP)XY]$_n$ wherein X and Y are nonchelating anionic ligands, for example, H, I, Br, Cl or F or noncoordinating or weakly coordinating anions, for example, BF$_4-$, ClO$_4-$, PF$_6-$ or BPh$_4-$ with X and Y being either the same or different, are especially effective when employed with a base such as a lower trialkylamine or an alkali metal hydroxide. Even when no base is employed and the temperature does not exceed 30° C. satisfactory results are obtained with this particularly preferred catalyst.

A preferred synthesis for naproxen involves the following reaction sequence, the subject asymmetric catalytic hydrogenation of this invention being conducted as a last step:

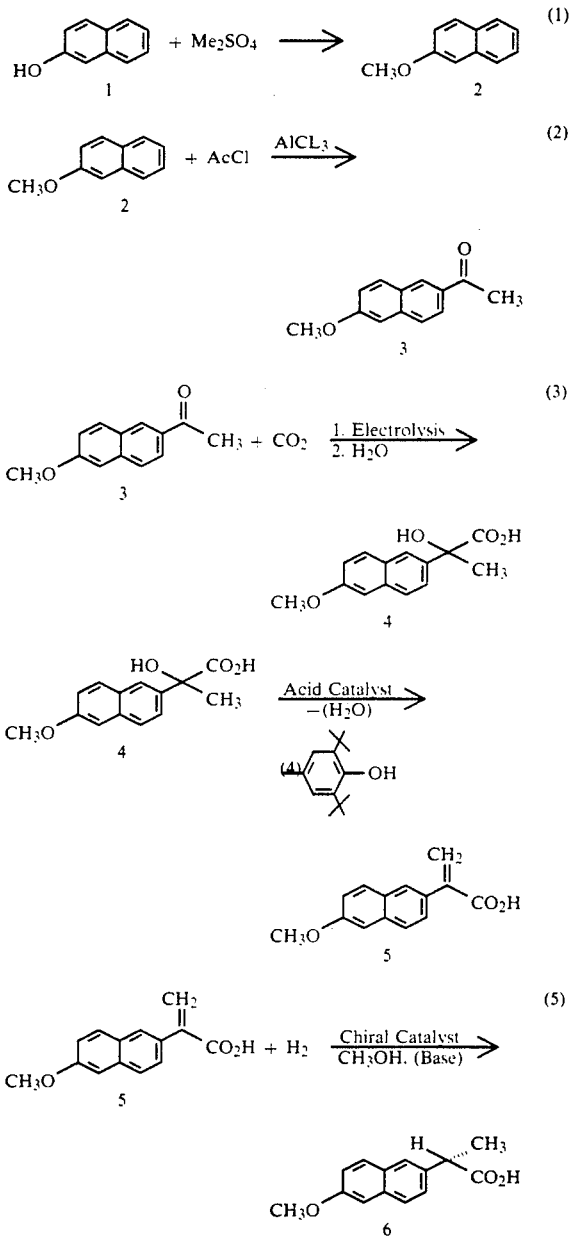

In this preferred synthesis, the first step is a typical Williamson ether synthesis involving reaction of 2-hydroxynaphthalene(1) with a methylating agent such as methyl sulfate to produce 2-methoxynaphthalene(2). Alternatively, 2-methoxynaphthalene is available commercially from Sigma-Aldrich.

The second step involves a Friedel Crafts acylation reaction of 2-methoxynaphthalene(2) to produce the corresponding 2-acetyl-6-methoxynaphthalene(3). Friedel Crafts acylation of naphthalene derivatives is a well known procedure as described in Jap. SHO-59-51234, which is incorporated herein by reference.

The third step involves electrochemical carboxylation of the acetyl moiety of 2-acetyl-6-methoxynaphthalene(3) followed by acid treatment to afford 2-(6'-methoxy-2'-naphthyl)-2-hydroxypropionic acid (4). As stated above, electrochemical carboxylation of aryl ketones followed by acid treatment is fully described in U.S. Pat. No. 4,601,797 to J. H. Wagenknecht, which is incorporated herein by reference.

Dehydration of (4) to produce 2-(6'-methoxy-2'-naphthyl)propenoic acid (5) is carried out in the fourth step utilizing propionic acid as both catalyst and solvent as previously described. Other acid catalysts, as previously described, may also be utilized.

Thus, in one aspect, the present invention is directed to a method of producing α-arylpropionic acids in high enantiomeric excess utilizing an asymmetric hydrogenation catalyst at temperatures below about 15° C. and, optionally, at pressures greater than about 75 psig $H_2$.

In another aspect, the present invention is directed to asymmetric catalytic hydrogenation of the dehydration product of an acid treated electrochemically carboxylated aryl ketone.

In another aspect, the present invention is directed to a method of preparing naproxen by catalytically asymmetrically hydrogenating the dehydration product of an acid-treated electrochemically carboxylated 2-acetyl-6-methoxynaphthalene.

In yet another aspect, the present invention is directed to catalytic asymmetric hydrogenation of 2-(6'-methoxy-2'-naphthyl)propenoic acid at temperatures below about 15° C. and, optionally, at pressures above about 75 psig $H_2$.

Contemplated equivalents of the catalysts and compounds set forth above, as well as the intermediates, are compounds otherwise corresponding thereto and having the same general properties with simple variations of the substituents. In addition, where a substituent is designated as, or can be, a hydrogen, the exact chemical nature of a substituent which is other than hydrogen at that position is not critical so long as it does not adversely affect the overall synthesis procedure.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily prepared from known starting materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

Optical yields were determined by either a standard optical rotation procedure or by chiral gas chromatography of the corresponding menthol (commercially available (+)-isomer obtained from Sigma-Aldrich) ester derivatives utilizing a CHIRASIL-VAL-L column obtained from Chrompack.

EXAMPLE 1

This example illustrates the effect of reaction temperature on the enantiomeric excess of the desired product obtained by catalytic asymmetric hydrogenation according to the teachings of the present invention.

A glass-lined stainless steel reactor was charged with 0.02 g of α-(6'-methoxy-2'-naphthyl) propenoic acid (prepared as in Example 3), 0.02 g triethylamine, 0.0003 g [Rh(COD)(DIPAMP)]BF$_4$ (prepared according to the procedure set forth in U.S. Pat. No. 4,142,992), and 4 g of methanol. The solution was stirred well with a magnetic stirrer at various temperatures and H$_2$ pressures for 16 hours. Results are reported in Table 1.

It should be noted that with this DIPAMP catalyst a decrease in temperature results in a significant increase in e.e. of the desired product. For example, comparing runs A and B, a decrease in temperature from 23° C. to 5° C. results in a 7% increase in e.e. Reducing the temperature another 10° C. to −5° C., as in run C, results in an 18.8% total increase in e.e. In addition, comparing runs a, d and e, an increase in pressure from 80 to 700 psig H* results in a 19% increase in e.e and an additional increase of 100 psig to 800 results in an overall increase in e.e. of 26%.

Comparing runs a and c, a combination of decreased temperature and increased pressure results in an 18% increase in e.e. with the DIOP catalyst. Similarly, comparing runs d and g, a combination of decreased temperature and increased pressure results in a 35% increase in e.e with the BINAP catalyst. In addition, a decrease in temperature without an increase in pressure results, as shown by comparing runs e and g and runs d and h, in an increase in e.e. ranging from 10% at higher pressures, i.e., 1000 psig, to 23% at nominal pressures of 200 psig.

TABLE 2

| Run | mg Precursor (mmol) | Catalyst | mg Cat. (mmol) | Temp (°C.) | Pressure (psig H$_2$) | Rxn Time (hrs) | e.e. (%) |
|---|---|---|---|---|---|---|---|
| a. | 50 (0.22) | [Rh(COD)((−)−DIOP)]ClO$_4$[1] | 6.2 (0.0077) | 25 | 45 | 16 | 73.1 |
| b. | " | " | " | 25 | 1000 | 16 | 79.2 |
| c. | " | " | " | −5 | 1000 | 16 | 86.3 |
| d. | 20 (0.088) | Ru(R-BINAP)(OAc)$_2$[2] | 1.3 (0.0015) | 25 | 200 | 16 | 66.5 |
| e. | " | " | " | 25 | 1000 | 65 | 81.5 |
| f. | " | " | " | −6 | 2000 | 14 | 88.0 |
| g. | " | " | " | −6 | 1000 | 19 | 89.7 |
| h. | " | " | " | −6 | 200 | 16 | 89.3 |

[1]Prepared according to the procedure set forth in J. Amer. Chem. Soc., 2397-2407 (1971) utilizing (−)−DIOP as the phosphine ligand and AgClO* as an anion source.
[2]Prepared according to the procedure set forth in J. Org. Chem., 52, 3174-76 (1987)

TABLE 1

| Run | Temp.[1] (°C.) | H$_2$ Press. (psig) | Enantiomeric Excess of α-(6'-methoxy-2'-naphthyl)propionic acid[1] |
|---|---|---|---|
| a. | 23 | 700 | 69 |
| b. | 5 | 700 | 74 |
| c. | −5 | 700 | 82 |
| d. | 23 | 800 | 73 |
| e. | 23 | 80 | 58 |

[1]Product recovered as the triethylammonium salt.

EXAMPLE 2

This Example illustrates the effect of temperature with different asymmetric hydrogenation catalysts. A 50 ml stainless steel autoclave with a glass liner and a magnetic stirring bar was charged with α-(6'-methoxy-2'-naphthyl)propenoic acid (prepared as in Example 3) in the amount indicated in Table 2, one equivalent of triethylamine, 3 g degassed methanol (solvent), and a catalyst as identified in Table 2 in the amount indicated. The solution was then stirred at the temperature and under the H$_2$ pressure indicated in Table 2 for the period indicated.

EXAMPLE 3

This example illustrates one embodiment for the synthesis of naproxen according to the teachings of the present invention.

Synthesis of 2-acetyl-6-methoxynaphthalene

A 2-liter, 3-neck flask equipped with a mechanical stirrer was charged with 700 mL nitrobenzene The solvent was cooled to ~10° C. with an ice bath, and into this was added 54.4 g aluminum trichloride (0.408 o mole) while the mechanical stirring was continued. After the AlCl$_3$ was dissolved, 56.5 g 2-methoxynaphthalene (0.36 mole) was added to the solution. The mixture was cooled to 5°–8° C. While the temperature was maintained at about 8° C., 33 g of acetyl chloride (0.42 mole) was added slowly to the mixture (in a period of about one hour). After all the acetyl chloride was added, the stirring at 8° C. was continued for 3 hours.

The stirring was stopped and the flask was placed in a constant temperature bath. The reaction mixture was allowed to stand at 40°±2° C. for 20 hours. The content of the flask was then poured into a large beaker which contained one liter of ice water and 100 mL concentrated HCl. The cold mixture was stirred with a magnetic stirrer for 30 minutes and then allowed to stand for 20 minutes for phase separation. (For easier phase separation, usually ~100 mL chloroform was added to the mixtures.)

The organic layer was collected and washed with dilute sodium bicarbonate solution and then ion-exchanged water (2-3 times, until neutral).

The organic solvents were stripped in a rotary evaporator and the residue was distilled in a Kugelrohr apparatus (0.5 mm Hg, 100°–120° C.). The crude yellow product (68 g) collected in the receiver was recrystalized in 100 mL hot methanol by cooling to ~5° overnight. The white crystals were filtered and washed with ~50 mL cold methanol twice. After drying in vacuo for 24 hours, 56 g pure 2-acetyl-6-methoxynathphalene (79% theoretical yield) was obtained. The methanol washing and the mother liquor were combined and evaporated to dryness. $^1$H NMR of the residue showed ~4 g 2-acetyl-6-methoxynaphthalene and ~5 g 1-acetyl-2methoxynaphthalene in it. These can be separated by further crystallization.

Synthesis of Hydroxynaproxen
(2-(6'-Methoxy-2'-Naphthyl)Lactic acid)

A one-liter reaction vessel was fitted with a 100 cm$^2$ lead cathode and a 100 cm$^2$ aluminum anode and a mechanical stirrer. Into this reactor were added 10 g of 2-acetyl-6-methoxynaphthalene, 15 g of tetrabutylammonium bromide (electrolyte), and 500 mL dry DMF. The mixture was stirred to make a homogeneous solution and then cooled to ~0° C. while dry $CO_2$ gas was bubbling through. After 30 minutes of $CO_2$ bubbling (to saturate the solution with $CO_2$), the constant current power supply was turned on and 0.6 A current (11 V) was allowed to pass the solution while the stirring and $CO_2$ bubbling was continued. The electrolysis was continued for 5 hours. After the shutoff of electricity and $CO_2$, the DMF solution was collected in a round-bottom flask. The solvent was stripped in a rotavac and the residue was shaken well with ~100 mL water for 3 hours. The solid material was filtered off and then stirred in 100 o mL water and 50 mL conc. HCl for 3 hours. The white solid was filtered and washed with 4 portions of ~30 mL water. The product was dried in vacuo for 3 days. Analysis of this dry powder indicated 8.8 g α-(6'-methoxy-2'-naphthyl)lactic acid product and 1.8 g 2-acetyl-6-methoxynaphthalene (starting material) in the solid material. The starting material was removed from the product by repeated washing with toluene.

Synthesis of 2-(6'-methoxy-2'-naphthyl)propenoic acid

A 250 mL round bottom flask was charged with 7.5 g α-(6'-methoxy-2'-naphthyl)lactic acid, 12.5 g fused potassium bisulfate, 0.007 g dilauryl thiodipropionate, 0.02 g 2,6-di-t-butyl-4-methylphenol, and 80 mL 1,2-dichlorobenzene (solvent). The mixture was stirred well at 160° C. for 3 hours and then filtered. The solid was washed with 100 mL hot methylene chloride and filtered. The filtrates were combined and evaporated to dryness in a rotavac. 95% yield of 2-(6'-methoxy-2'-naphthyl) propenoic acid was obtained.

Hydrogenation of 2-(6'-methoxy-2'-naphthyl)propenoic acid

A 100 mL stainless steel autoclave was charged with 5 g 2-(6'-methoxy-2'-naphthyl)propenoic acid, 2.2 g triethylamine, 0.04 g [Ru$_2$Cl$_4$(S-BINAP)$_2$]NEt$_3$, and 80 mL o methanol under nitrogen atmosphere. The mixture was stirred well under 800 psig H$_2$ at −2° C. for 16 hours. Analysis of the product solution indicated quantitative chemical yield of Naproxen with 96% e.e. It is contemplated that the actual time to completion may be shorter.

EXAMPLE 4

This example illustrates the extremely high e.e.s obtained utilizing the chloro-Ru-BINAP catalyst complexes and illustrates the best mode for conducting the asymmetric hydrogenation of α-arylpropenoic acids with such catalyst. The first two catalysts listed in Table 3 were prepared according to the procedure set forth in EP 0272787 A2 and all catalysts were utilized with molar ratios of substrate/catalyst/solvent/amine similar to those of Example 3. Thus, a ruthenium chloride derivative is reacted with cycloocta-1,5-diene (COD) in an ethanol solution and one mole of the resulting complex is reacted with 1.2 moles of the desired BINAP derivative under heating and in a solvent such as toluene or ethanol in the presence of 4 moles of a tertiary amine such as triethylamine. All hydrogenations were conducted in the presence of triethylamine (1 m/m) except as noted.

TABLE 3

| Catalyst | Press. (psig H$_2$) | T(°C.) | Reaction t (hrs) | % e.e. |
|---|---|---|---|---|
| RuHCl(BINAP)$_2$ | 500 | −6 | 14 | 97.7 |
| [Ru$_2$Cl$_4$(BINAP)$_2$](NEt$_3$) | 500 | −7 | 91 | 98.1 |
| Ru(Benzene)Cl$_2$+BINAP$^1$ | 500 | −6 | 14 | 97.2 |
| Ru(DMSO)$_4$Cl$_2$+BINAP$^1$ | 500 | −4 | 62 | 97.5 |
| Ru(COD)Cl$_2$+BINAP+NEt$_3$$^2$ | 100 | −5 | 16 | 94.4 |
| Ru(COD)Cl$_2$+BINAP+NEt$_3$$^2$ | 1000 | −5 | 16 | 97.1 |
| Ru(COD)Cl$_2$+BINAP+NEt$_3$$^{2,3}$ | 1000 | −5 | 16 | 92.2 |
| Ru(COD)Cl$_2$+BINAP+NEt$_3$$^{2,3}$ | 1000 | 25 | 16 | 91.7 |

$^1$Refluxed in toluene for 16-20 hrs. and utilized in situ.
$^2$Stirred in toluene @ 120° C. for 10 hrs. solvent evaporated and residue washed with MeOH and then dried in vacuo.
$^3$Hydrogenation conducted in absence of triethylamine.

EXAMPLE 5

This example illustrates the temperature and pressure effects on the e.e. utilizing [Ru$_2$Cl$_4$(BINAP)$_2$](NEt$_3$) (under conditions similar to those of Example 4) in the presence of triethylamine to hydrogenate 2-(6'-methoxy-2'-naphthyl)propenoic acid, prepared as in Example 3. Results are reported in Table 4.

TABLE 4

| Pressure (psig H$_2$) | T (°C.) | Reaction t (hr.) | % e.e. |
|---|---|---|---|
| 100 | −7 | 91 | 95.3 |
| 200 | " | " | 96.7 |
| 500 | " | " | 98.1 |
| 2000 | " | " | 98.5 |
| 100 | 11 | 15 | 85.0 |
| 200 | " | " | 89.8 |
| 500 | " | " | 95.2 |
| 1000 | " | " | 95.4 |
| 100 | 25 | 16 | 70.6 |
| 200 | " | " | 82.6 |
| 500 | " | " | 90.1 |
| 1000 | " | " | 93.3 |

EXAMPLE 6

This example illustrates the temperature and pressure effects on e.e. for naproxen utilizing Ru(BINAP)(OAc)$_2$ in the presence of triethylamine as catalyst (prepared according to the procedure of Noyori et al) under conditions similar to those of Example 5. Results are reported in Table 5.

TABLE 5

| | Pressure (psig H$_2$) | T (°C.) | Reaction t (hr.) | % e.e. |
|---|---|---|---|---|
| a. | 200 | −6 | 16 | 89.3 |
| b. | 1000 | −6 | 19 | 89.7 |
| c. | 2000 | −6 | 14 | 88.0 |
| d. | 200 | 25 | 16 | 66.5 |
| e$^1$. | 1000 | 25 | 16 | 83.9 |
| f. | 1000 | 25 | 65 | 81.5 |
| g. | 1800 | 28 | 14 | 84.7 |

$^1$Conducted in the absence of triethylamine.

EXAMPLE 7

This example illustrates the effectiveness of the use of a base in the asymmetric hydrogenation of α-arylpropenic acids. The results are given in Table 6.

TABLE 6

| Catalyst | Pressure (psig $H_2$) | T (°C.) | Reaction Time (hours) | Base | % Conv. | % e.e. |
| --- | --- | --- | --- | --- | --- | --- |
| $[Ru(S-BINAP)I_2]_n$ | 1000 | −3 | 16 | Triethylamine | 100 | 96 |
| $[Ru(S-BINAP)Br_2]_n$ | " | " | " | " | " | " |
| $[Ru(S-BINAP)Cl_2]_n$ | " | " | " | " | " | " |
| $[Ru(S-BINAP)(BF_4)_2]_n$ | " | " | " | " | " | 98 |
| $[Ru(S-BINAP)F_2]_n$ | " | 0 | " | " | 95 | 96 |
| $[Ru(S-BINAP)F_2]_n$ | " | " | " | None | 100 | 93 |
| $[RuCl_2(S-BINAP)]_21.NEt_3$ | " | −5 | " | Triethylamine | " | 97.1 |
| $[RuCl_2(S-BINAP)]_2.NEt_3$ | " | " | " | None | " | 92.2 |
| $[Ru(S-BINAP)(benzene)Cl]Cl$ | " | 0 | 14 | " | 37 | 86.4 |
| $[Ru(S-BINAP)(benzene)Cl]Cl$ | " | " | " | Triethylamine | 61 | 98.4 |
| $([Ru(S-BINAP)][BF_4]_2)_n$ | " | −3 | 64 | None | 65 | 87 |
| $([Ru(S-BINAP)][BF_4]_2)_n$ | " | " | " | Triethylamine | 75 | 95 |

EXAMPLE 8

This example shows the hydrogenation of 2-(p-isobutylphenyl)propenoic acid to produce 2-(pisobutylphenyl)propionic acid using the general s hydrogenation procedure of Example 3. The catalyst was $[RuCl_2(S-BINAP)]_2NEt_3$ and the base was triethylamine. In each run the yield of 2-(p-isobutylphenyl)propionic acid (as the triethylammonium salt) was 100%. The results are reported in Table 7.

TABLE 7

| | Pressure (psig $H_2$) | T (°C.) | Reaction t (hr.) | % e.e. |
| --- | --- | --- | --- | --- |
| a. | 100 | −5 | 24 | 88 |
| b. | 100 | 25 | 24 | 71 |
| c. | 1000 | −5 | 24 | 96 |
| d. | 1000 | 25 | 24 | 87 |

EXAMPLE 9

This example illustrates the preferred method for catalytically dehydrating hydroxynaproxen and compares such preferred method to a well-known method.

A. Preferred Method 1

A 100 mL round-bottomed flask magnetic stirring bar was charged with 0.5 g of hydroxynaproxen and 10 mL of acetic acid. The mixture was refluxed with magnetic stirring for 4 hors. Evaporation of the acetic acid gave 0.44 g of white dehydronaproxen in 95% yield.

Preferred Method 2

A 100 mL round-bottom flask with a magnetic stirring bar was charged with one gram of hydroxynaproxen and 10 mL propionic acid. The mixture was magnetically stirred at reflux temperature for two hours. Evaporation of the solvent in vacuo gave 0.88 g dehydronaproxen (95% yield) with little discoloration.

B. Known Method

A 100 mL round-bottomed flask with a s magnetic stirring bar was charged with 0.5 g hydroxynaproxen, 2.5 g fused potassium acid sulfate (catalyst), and 10 mL ortho-dichlorobenzene (solvent). The mixture was refluxed with magnetic stirring for four hours. The resulting solution was deep red. The mixture was filtered while still hot with a hot filtering funnel. The filtrate was evaporated to dryness. The dehydronaproxen product (0.44 g, 95% yield) was of undesirable deep red color. To clear up this color, decoloration with activated carbon and repeated crystallation were required. A substantial product loss was observed during this clean-up process.

EXAMPLE 10

Synthesis of Hydroxynaproxen (2-[6'-Methoxy-2'-Naphthyl]Lactic Acid) Via Electrocarboxylation A reaction vessel was fitted with a 400 cm² lead cathode and a similar-sized aluminum anode. A reaction solution was prepared by dissolving 36 g 2-acetyl-6-methoxynaphthalene and 60 g tetrabutylammonium bromide in 1.8 liter N,N-dimethylformamide (DMF). The solution was continuously circulated through the reaction vessel at a rate of about 4 gallons per minute by using a circulation pump. The reaction system was pressurized with carbon dioxide and about 40 psig $CO_2$ pressure was maintained throughout the reaction. A direct current of six ampere was applied to the system and the reaction was carried out at 40°–42° C. for 1.5 hours. Analysis of the product after hydrolysis indicated 80% conversion of the 2-acetyl-6-methoxynaphthalene with 95% selectivity for the desired hydroxynaproxen.

EXAMPLE 11

Catalytic Dehydration of 2-(4-Isobutylphenyl)-2-Hyroxypropionic Acid

A 250 mL round-bottomed flask was charged with 0.5 g 2-(4-isobutylphenyl)-2-hydroxypropionic acid, 5 g fused potassium bisulfate, 0.001 g 1,6-di-t-butyl-4-methylphenol, and 100 mL chlorobenzene. The mixture was stirred with a magnetic stirring bar at 130° C. for two days. ¹H NMR analysis of the resulting product indicated 100% conversion of the starting material to the desired 2-(4-isobutylphenyl)propenoic acid.

It is contemplated that utilization of other asymmetric hydrogenation catalysts such as complexes of other optically active bis phosphine compounds, biaryl compounds and binaphthyl compounds will produce similar results when utilized according to the teachings of the present invention.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. Process for preparing naproxen comprising:
   a) electrochemically carboxylating 2-acetyl-6-methoxy-naphthalene to afford 2-(6'-methoxy-2'-naphthyl)-2-hydroxypropionic acid;
   b) dehydrating the 2-(6'-methoxy-2'-naphthyl)-2-hydroxypropionic acid of step a) to afford 2-(6'-methoxy-2'-naphthyl)propenoic acid; and
   c) catalytically asymmetrically hydrogenating the 2-(6'-methoxy-2'-naphthyl) propenoic acid of step b).

2. Process of claim 1 wherein Step b) is conducted in a low molecular weight carboxylic acid selected from acetic acid and propionic acid.

3. Process of claim 1 wherein Step c) is conducted utilizing a ruthenium asymmetric hydrogenation catalyst at a temperature of less than about 30° C.

4. Process of claim 3 wherein the catalyst is represented by the formula:

[Ru(BINAP)XY]$_n$ wherein X and Y represent a nonchelating anionic ligand or a noncoordinating anion.

5. Process of claim 3 wherein the temperature is less than about 15° C.

6. Process of claim 1 wherein said 2-acetyl-6-methoxynaphthalene is obtained by a Friedel Crafts acylation of 2-methoxynaphthalene.

7. Process of claim 6 wherein said 2-methoxynaphthalene is obtained by Williamson ether synthesis utilizing a methylating agent and 2-hydroxynaphthalene.

8. A process for preparing an α-arylpropionic acid comprising:
   (a) electrochemically carboxylating an α-arylketone to produce an 2-aryl-2-hydroxypropionic acid,
   (b) dehydrating said 2-aryl-2-hydroxypropionic acid to produce an α-arylpropenoic acid, and
   (c) catalytically asymmetrically hydrogenating said α-arylpropenoic acid to produce said α-arylpropionic acid.

9. The process of claim 8 wherein the dehydration of said 2-aryl-2-hydroxypropionic acid is conducted in a low molecular weight carboxylic acid selected from the group consisting of acetic acid and propionic acid.

10. The process of claim 8 wherein the catalytic asymmetric hydrogenation of said α-arylpropenoic acid is conducted utilizing a ruthenium asymmetric hydrogenation catalyst selected from the group consisting of optically active bisphosphine binaphthyl compounds of the formula Ru(BINAP)(OCOR)$_2$, Ru$_x$H$_y$Cl$_z$(BINAP)$_2$(S)$_p$ and [Ru(BINAP)XY]$_n$, wherein BINAP represents a tertiary phosphine of the formula:

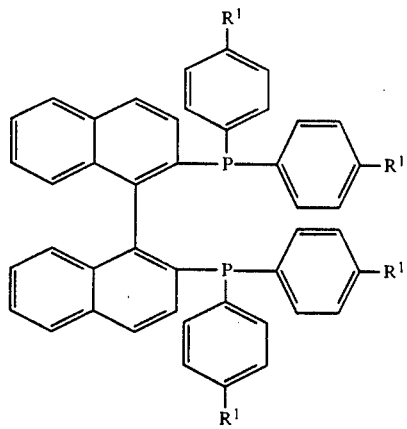

R represents substituted and unsubstituted alkyl radicals having 1 to about 6 carbon atoms, substituted and unsubstituted halogenated alkyl radicals having 1 to about 6 carbon atoms, and substituted or unsubstituted aryl, arylkyl and arlkaryl radicals, R' represents hydrogen, substituted or unsubstituted alkyl radicals having 1 to about 6 carbon atoms, and substituted or unsubstituted aryl, aralkyl and alkaryl radicals, S is a tertiary amine, X and Y independently represent a nonchelating anionic ligand or a noncoordinating anion, y is 0 or 1, and when y=0, x=2, z=4 and p=0 or 1, and when y=1, x=1, y=1 and p=0, and wherein said catalytic asymmetric hydrogenation is conducted at a temperature of less than about 30° C.

11. The process of claim 10 wherein said catalytic asymmetric hydrogenation is conducted in the presence of a base.

12. The process of claim 10 wherein said catalyst is represented by the formula: [Ru(BINAP)XY]$_n$ wherein X and Y independently represent a nonchelating anionic ligand or a noncoordinating anion.

13. The process of claim 10 wherein said temperature is less than about 15° C.

14. The process of claim 8 wherein said α-arylpropionic acid is selected from the group consisting of naproxen, ibuprofen, ketoprofen, pirprofen, fenoprofen, suprofen, flurbiprofen, benoxaprofen and carprofen.

15. The process of claim 14 wherein said α-arylpropionic acid is selected from the group consisting of naproxen and ibuprofen.

* * * * *